(12) United States Patent
Richardson

(10) Patent No.: US 10,537,179 B2
(45) Date of Patent: Jan. 21, 2020

(54) INTENSIVE USE ROCKING CHAIR

(71) Applicant: Jed C. Richardson, Batavia, IL (US)

(72) Inventor: Jed C. Richardson, Batavia, IL (US)

( * ) Notice: Subject to any disclaimer, the term of this patent is extended or adjusted under 35 U.S.C. 154(b) by 0 days.

(21) Appl. No.: 15/582,603

(22) Filed: Apr. 29, 2017

(65) Prior Publication Data
US 2018/0325262 A1 Nov. 15, 2018

(51) Int. Cl.
| | | |
|---|---|---|
| A47C 3/12 | (2006.01) | |
| A47C 3/029 | (2006.01) | |
| A47C 7/72 | (2006.01) | |
| A47C 31/12 | (2006.01) | |
| A47C 7/74 | (2006.01) | |
| A47C 31/00 | (2006.01) | |
| A47C 7/70 | (2006.01) | |
| A61B 5/00 | (2006.01) | |
| A61B 5/024 | (2006.01) | |
| A47C 1/02 | (2006.01) | |
| A47C 7/40 | (2006.01) | |

(52) U.S. Cl.
CPC .............. *A47C 3/029* (2013.01); *A47C 3/12* (2013.01); *A47C 7/705* (2018.08); *A47C 7/72* (2013.01); *A47C 7/725* (2013.01); *A47C 7/727* (2018.08); *A47C 7/74* (2013.01); *A47C 7/742* (2013.01); *A47C 7/748* (2013.01); *A47C 31/008* (2013.01); *A47C 31/12* (2013.01); *A47C 1/02* (2013.01); *A47C 7/40* (2013.01); *A61B 5/024* (2013.01); *A61B 5/6891* (2013.01)

(58) Field of Classification Search
CPC ......... A47C 3/029; A47C 7/705; A47C 7/727; A47C 3/12; A47C 7/72; A47C 7/725; A47C 7/74; A47C 7/742; A47C 7/748; A47C 31/008; A47C 31/12
USPC .................. 297/258.1–272.4, 217.4, DIG. 7
See application file for complete search history.

(56) References Cited

U.S. PATENT DOCUMENTS

| 68,624 | A | * | 9/1867 | Hoffman | ................ F16B 43/00 411/544 |
|---|---|---|---|---|---|
| 1,303,994 | A | * | 5/1919 | Ulmann | ............... A47C 1/0345 297/271.1 |
| 2,246,057 | A | * | 6/1941 | Michaelis | ............. A47C 3/021 297/287 |
| 2,612,936 | A | * | 10/1952 | Lansaw | ................. A47C 3/029 297/271.6 |

(Continued)

*Primary Examiner* — Syed A Islam
(74) *Attorney, Agent, or Firm* — James D Palmatier; Applied Patent Services

(57) ABSTRACT

The invention is a rocker for therapeutic treatment of a user by control of actuators in the rocker and sensing biometric and mechanical conditions of and around the user. The rocker may be formed of a unitary body of translucent or transparent material. The body of the chair features a single tail floor engagement portion and a user area of seat and back. The rocker may have actuators mounted in or near the rocker to generate heat, sound, vibration or light, Sensors in and around the chair monitor movement of the rocker and biometric conditions of the user. A control panel in communication with the actuator and sensors controls and monitors conditions and communicates with a monitoring computer for storage and reporting. Predetermined patterns of actuator activation may be programmed into the computer for transmission and execution by the control panel.

17 Claims, 4 Drawing Sheets

(56) References Cited

U.S. PATENT DOCUMENTS

| | | | | |
|---|---|---|---|---|
| 3,526,429 A | * | 9/1970 | Metzger | A47C 3/029 297/271.5 |
| 3,669,490 A | * | 6/1972 | Bertolet | A47C 3/029 248/345.1 |
| 4,141,588 A | * | 2/1979 | Anderson | A47D 13/102 297/271.5 |
| 4,258,952 A | * | 3/1981 | Dutra | A47C 3/029 248/364 |
| 4,640,546 A | * | 2/1987 | Aguilar | A47C 3/02 297/259.2 |
| 5,090,769 A | * | 2/1992 | Wade | A47C 3/029 297/258.1 |
| 6,361,106 B1 | * | 3/2002 | Huang | A47D 13/107 297/16.1 |
| 6,412,867 B2 | * | 7/2002 | Robinson | A47C 3/029 297/135 |
| 8,622,473 B2 | * | 1/2014 | Walsh | A47C 3/021 297/287 |
| 8,801,098 B1 | * | 8/2014 | Richards | A47C 3/029 297/260.2 |
| 2008/0111408 A1 | * | 5/2008 | Duran | A47C 7/72 297/217.4 |
| 2010/0032995 A1 | * | 2/2010 | Tarter | A47G 23/0216 297/188.01 |
| 2012/0086249 A1 | * | 4/2012 | Hotary | B60N 2/809 297/284.3 |
| 2018/0271288 A1 | * | 9/2018 | Fletcher | A47C 3/029 |

* cited by examiner

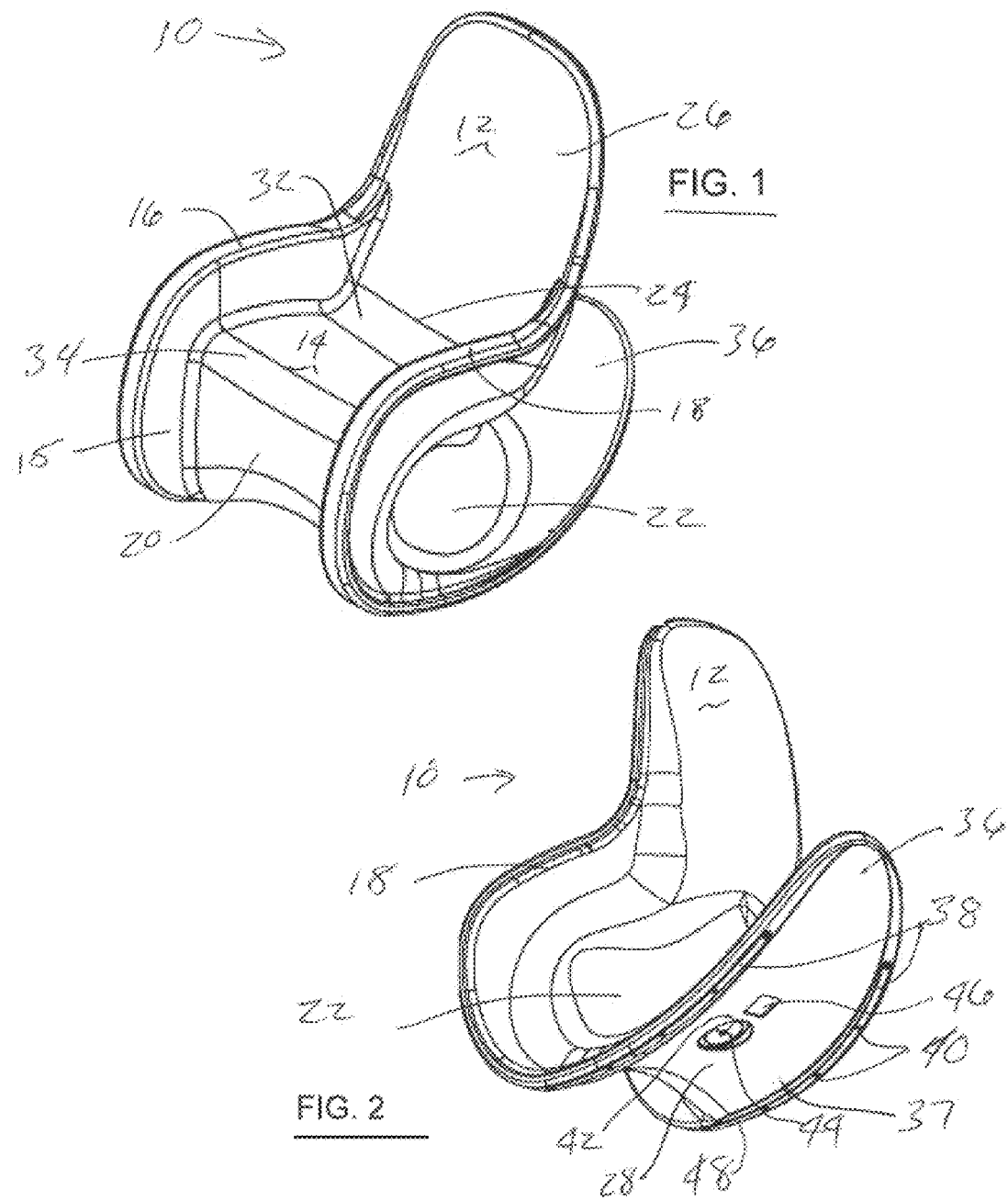

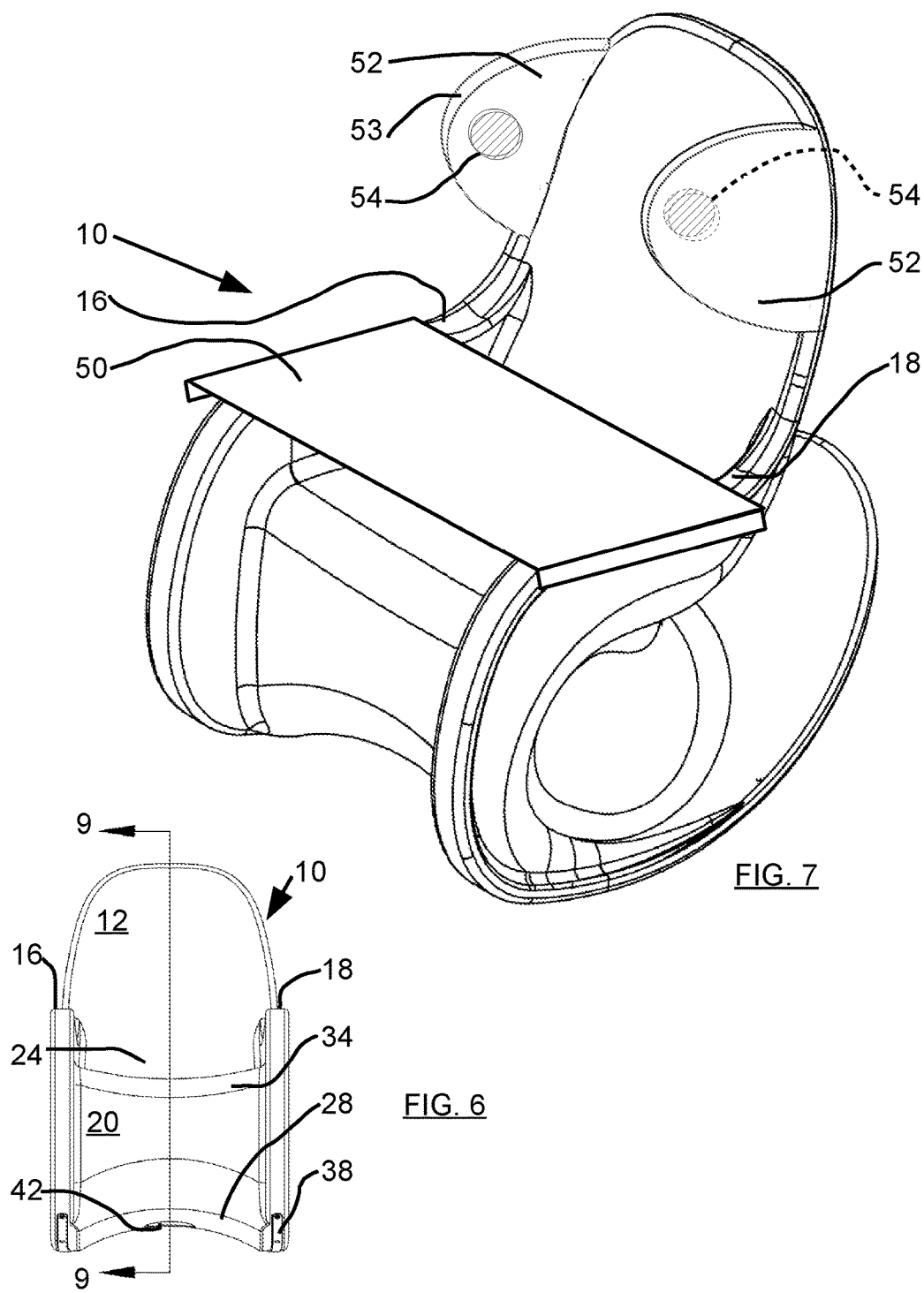

INTENSIVE USE ROCKING CHAIR

FIELD OF THE INVENTION

The present invention relates generally to furniture for use in intensive use applications specifically therapeutic treatment of individuals in these environments and the like.

BACKGROUND OF THE INVENTION

Intensive use chairs and seating arrangements have been designed for use in demanding environments to provide therapeutic help for individuals. Such environments may include facilities housing individuals for rehabilitation from health or legal problems that require therapeutic devices such as chairs for safely furnishing living quarters while being durable. Prior art therapeutic seating devices include stationary, reclining and rocking chairs having massage, muscle exercise, and heat applying facilities built into the chair. Such chairs are typically constructed of materials such as metal, wood, fiberglass and plastic and formed as predesigned units.

Assembled furniture may present certain hazards in use in treatment or incarceration settings where furniture components may be removed and turned into weapons. Fasteners may be removed and used to inflict harm on the patient or others. Plastics and fiberglass construction has replaced wood and metal by its ability to be formed into three-dimensional shapes. Fiberglass offered a more appealing aesthetic than steel or wood, and more resistant to damage by the user and damage by bodily fluids. Fiberglass may crack or splinter creating pieces or shards usable as weapons and may also degrade with time.

Intensive use chairs for such facilities require durability and ease of cleaning. Unitary manufacture of the chair to reduce pieces and fasteners and help avoid disassembly. Furthermore, ballasting is desirable to make the chair difficult to move. Unitary design reduces crevices and openings to reduce the opportunity to conceal items such as drugs, weapons or other contraband. Integral manufacturing such as rotational molding may reduce assembly and seal functional components in the chair. Ballasting in a hollow, roto-molded chair makes the furniture more difficult to move and lift.

Therefore, it is desirable to provide an integral molded therapeutic chair having durability, aesthetically pleasing characteristics and design for comfortable use that has therapeutic features integrated into the chair for treating and monitoring a user.

BRIEF SUMMARY OF ONE EMBODIMENT OF THE INVENTION

One embodiment of the present invention is directed to a rocking chair adapted to provide movement such as rocking to provide the user with movement as a therapeutic means. The chair may be molded as a unitary hollow chair body having access to the inside of the hollow body for device placement and ballasting. The rocking chair may be molded having hollow body, the body comprising a seat, a back, two opposing arms, a knee rest, leg rest and a base. The seat between the knee rest and the back, The rocking chair back may have a lumbar zone, head zone and shoulder zone between the lumbar zone and head zone. The hair leg rest may have a calf zone and a foot zone. The chair bottom is adapted to engage the floor and accommodate the user rocking forward and backward as in a traditional rocking chair. The base on the chair bottom may have arcuate runners to engage the floor and accommodate the movement of the chair. A limit stop may be disposed on the runners to prevent the chair from tipping over in a front or back rocking movement.

The hollow body provides a cavity in the chair adjacent the back, seat and arm rests. The hollow body may be roto-molded out of a translucent, transparent or solid color plastic. Actuators and sensors may be disposed in the hollow cavity to provide therapeutic actions and to measure user parameters for feedback to the practitioner. Actuators may include light, vibration, heating/cooling and sound. Light control in a translucent or transparent chair body is provided to illuminate the chair and thus the surrounding environment in predetermined colors. The light control may control the light source to illuminate the chair in a steady state or strobe like pattern at constant or varying intensity to create a predetermined light environment for therapeutic treatment. Vibration, heating, and cooling may be provided in one or more of the predefined zones on the chair. Sound may be sourced from outside the chair and projected by speakers located in a predefined zone on the chair.

Sensors such as thermocouple, accelerometers and biometric sensors may be disposed in the hollow body or on the outer surface to monitor the user in a predetermined zone on the chair. Sensors provide feedback to an actuator control and monitoring module for storage and reporting to a therapeutic practitioner. Sensor information may be stored on the chair for analysis. Sensor feedback may be processed by the actuator control unit attached to rocker to analyze user reaction to the actuator outputs. The data from sensors may also be used to calculate actuator control. Sensors may be used to gather user data such as the amount of time rocking, frequency, rigorousness; and vital signs such as respiration, heart rate and body temperature for logging and analysis.

The rocker may further comprise an isolation panel removably on the back adjacent a head supporting portion. The isolation panel serves as blinders on a horse to limit peripheral vision of a user. The isolation panel may further comprise speakers integrated therein. The speakers attached to a control panel for creating sound for noise canceling or recreation of music or speech.

The above description sets forth, rather broadly, the more important features of the present invention so that the detailed description of the preferred embodiment that follows may be better understood and contributions of the present invention to the art may be better appreciated. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE SEVERAL VIEWS OF THE DRAWING

FIG. 1 is a top perspective view of a first embodiment of the present invention.

FIG. 2 is a bottom perspective view of a first embodiment of the present invention.

FIG. 6 is a front elevation view of a first embodiment of the present invention.

FIG. 7 is a front perspective view of a second embodiment of the present.

DETAILED DESCRIPTION OF THE INVENTION

Figure 3:
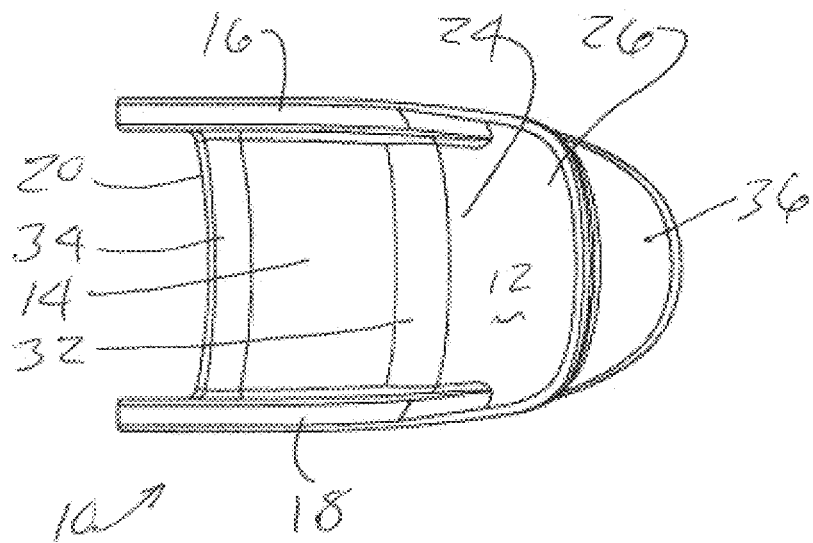
FIG. 3 is a top plan view of a first embodiment of the present invention.
Figure 4:
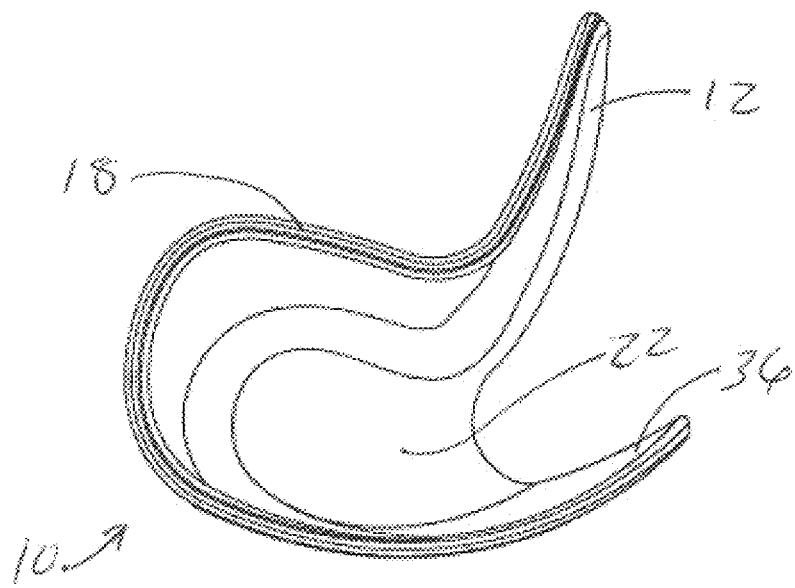
FIG. 4 is a side elevation view of a first embodiment of the present invention.
Figure 5:
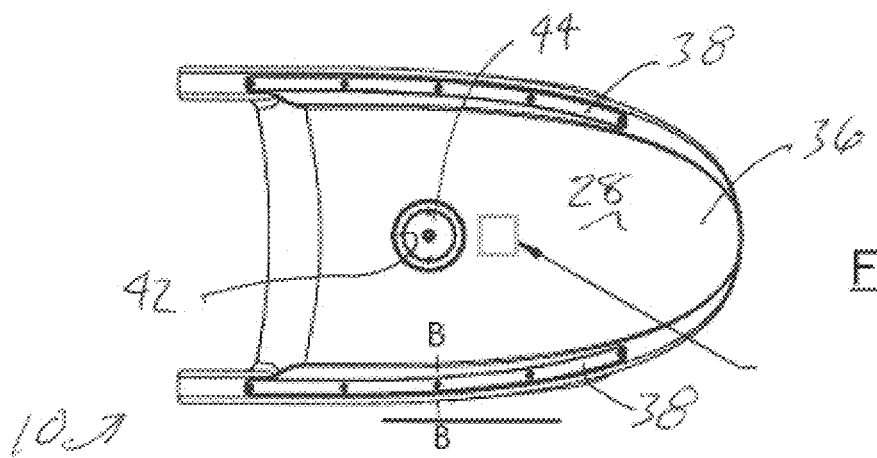
FIG. 5 is a bottom plan view of a first embodiment of the present invention.
Figure 8:
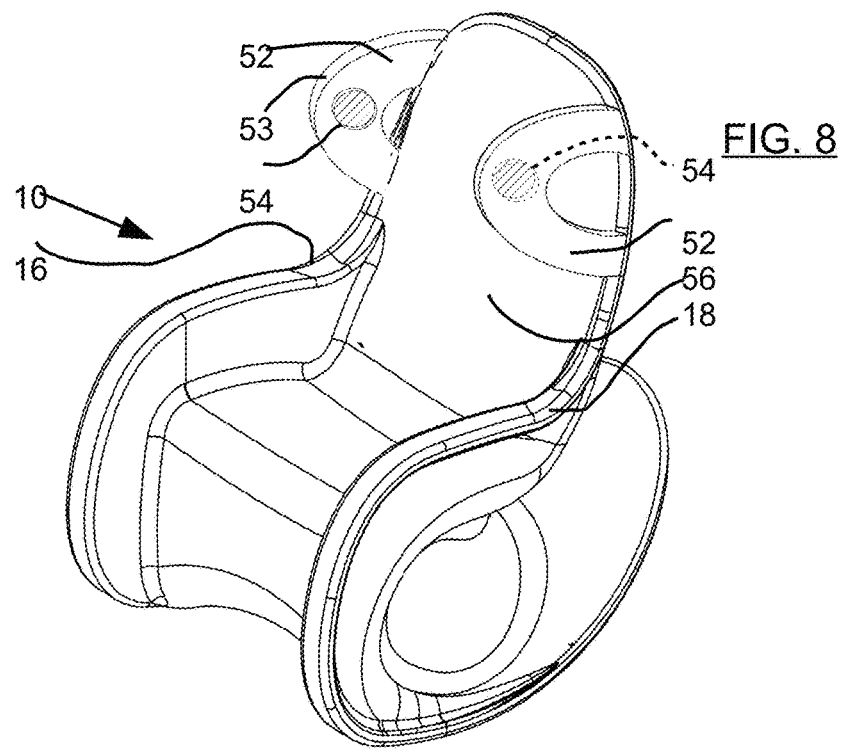
FIG. 8 is a perspective view of the second embodiment of the present invention.

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Referring to FIG. 1, the rocker 10 may have a one piece, hollow body 15 comprising a back 12, a seat 14, a first arm rest 16 and a second arm rest 18. The front 20 of the rocker 10 extends from the seat 14 to the base 22. The seat 14 may include a hip portion 32 and a knee rest 34. The base 22 comprises a bottom wall 28 and a tail 36. Extended edges 37 may adapted to extend from the bottom wall 28 and hold the bottom wall 38 off the floor surface. Runners 38 may be disposed on extended edge surfaces 37 to engage the floor surface. The runners 38 made of a wear resistant material such as nylon. The back 12 comprises a lumbar section 24 and a shoulder section 26. The tail 36 extending from the base 22. The tail 36 having a curved shape adapted to limit a rocking angle defined by the deflection of the seat 14 from a horizontal position.

Referring to FIGS. 2-6, rocker 10 has a hollow body 15 extending from the back 12 to the tail 36. Base 22 comprises a bottom wall 28 sealing the hollow body 15. Bottom wall 28 may have access port 42 formed there through providing outside access to the hollow body 15. Access port 42 may be closed by ballast cover 44. A logo indentation 46 maybe formed on bottom wall 28. Runners 38 are attached by fasteners 40 which may be a tamper-resistant (pin-in-Torx Drive) screw type. Ballast cover 44 may be fixed into place by welding, adhesives or other means.

Referring to FIG. 7, rocker 10 may further comprise tray 50 extending from first armrest 16 to second armrest 18 across seat 14. Isolation panel 52 maybe this disposed on back 12 adjacent to or above shoulder section 26. The isolation panel 52 may have blinder flaps 53 extending from the back 12 and over the arm rests 16, 18 to limit peripheral sight of the user. Isolation panel 52 may have speakers 54 mounted therein or on flaps 53. Speakers 54 may be energized to create music, sound or noise canceling energy. The isolation panel 52 may be removable.

Figure 9:
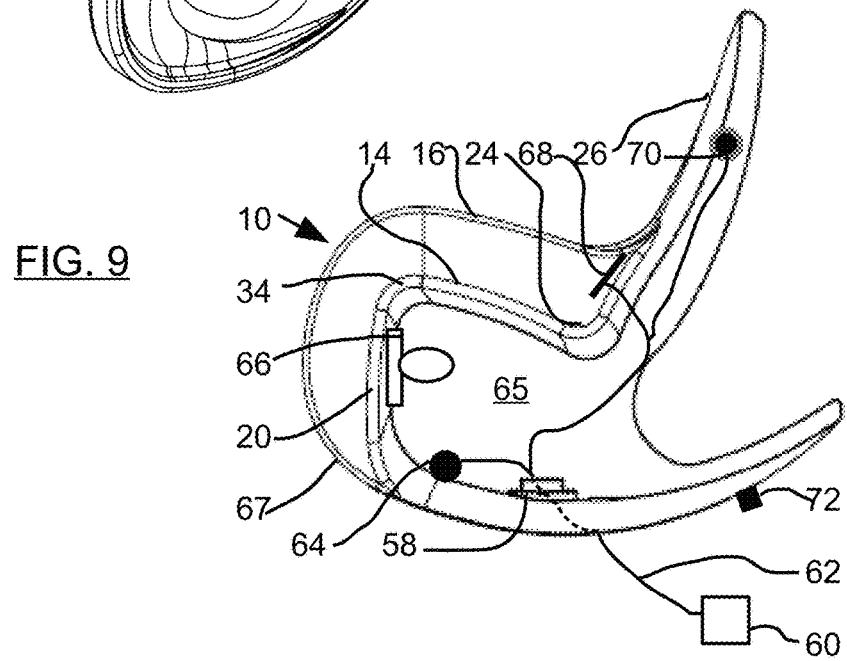
FIG. 9 is a section view of the first embodiment of the present invention taken at approximately 9-9 of FIG. 6.

Referring to FIG. 9, rocker 10 may further comprise a control panel 58 attached to an external Monitor and log computer 60 by a communication link 62. Computer 60 may have software adapted to provide a time base for sensor information gathering and a schedule for actuator control. Computer 60 may be adapted to store scheduled actuator control and gathered sensor information for reporting. Communication link 62 maybe a wireless or wired connection. Communication link 62 may also be used to provide power to control panel 58. Control panel 58, may be located in the hollow body 15. Control panel 58 may have communications with outside monitor 60 and provide control and power to sensors 64 and actuators 70 in and on rocker 10. Hollow body 15 may have a ballast chamber 65 extending throughout the hollow body 15. Ballast chamber 65 is the interior of hollow body 15. Movement sensor 64 may be disposed in ballast chamber 65 in areas such as adjacent to the base 22 or the back 12. Movement sensors 64 such as an accelerometer 64 may sense and calculate movement angle, velocity and acceleration as well as frequency of rocking action. Movement sensors 64 may be attached to control panel 58. Light source 66, such as LED or incandescent bulb, may be mounted in ballast chamber 65 to generate light. The hollow body 15 may have a shell 67 formed of a translucent or transparent material whereby light may be transmitted through the shell 67 and into the ambient environment adjacent rocker 10 for sensing by the user. Shell 67 material may be translucent or transparent type plastic material as is known in rotoforming plastic objects. Control panel 58 may be used to control lights 66 to provide steady or oscillating type light intensity of either white or colored light. Lights are 66 may be placed anywhere within the hollow body 15.

Continuing to refer to FIG. 9, biometric sensor 68 may be disposed on the outside of the body 15 for direct engagement with a user (not shown) sitting on the rocker 10 or inside the ballast chamber. A biometric sensor 68 may be used to sense temperature, blood flow, pulse and other biometrics parameters. Noise generators 70 maybe disposed in hollow body 15 to create sound or vibration for therapeutic means. Noise generators 70 may be a pulse generator or speaker 54 connected to control panel 58. Noise generators 70 may be used to create heat, or vibratory patterns up to and including sound for therapeutic treatment of the patient. A rocker stop 72 may be disposed on the runners 38 or on the tail 36 to limit the rocking angle of rocker 10 to prevent overturning where the back 12 may hit the floor surface.

In use, the rocker 10 may be programmed for a predetermined sequence of sensory engagements by the control panel 58 connected to such actuators to generate stimulation of the user. The actuators 66, 70, may generate stimulus by light, sound vibration, heat and or cooling. Sensors 64, 68 may be connected on or in rocker 10. Sensors 64, 68 may be connected to and in communication with the control panel 58 for detecting and reporting mechanical and biometric conditions. The control panel 58 may be in communication with outside monitor 60 to record and report sensed conditions in coordination with generated stimulations by actuators 66, 70. Control panel 58 may be disposed on the rocker 10, in the ballast chamber 65 or outside the hollow body 15. Control panel 58 may have communication with sensors and actuators in and on the rocker 10 for controlling, monitoring sensors and actuators thereby providing a therapeutic environment for a user while recording sensed conditions.

Although the description above contains many specifications, these should not be construed as limiting the scope of the invention but as merely providing illustrations of some of the embodiments of this invention. Thus, the scope of the invention should be determined by the appended claims and their legal equivalents rather than by the examples given. Further, the present invention has been shown and described with reference to the foregoing exemplary embodiments. It is to be understood, however, that other forms, details, and embodiments may be made without departing from the spirit and scope of the invention which is defined in the following claims.

I claim:

1. A rotomolded rocking chair for use on a floor comprising:
    a hollow body comprising a hollow base, and a hollow back, the hollow base further comprises a seat, a front wall, a first and second arm rests, a bottom wall and a tail, the hollow base on the hollow back, the seat on top of the hollow base adjacent the hollow back, the front wall extending down from the seat, the front wall attached to and extending between the first and second arm rests, the front wall on the bottom wall, the first arm rest spaced from the second arm rest, the bottom wall spaced from the seat, the first arm rest on the seat, the first arm rest comprising a first extended edge on the bottom wall, the second arm rest on the seat, the second arm rest comprising a second extended edge on the bottom wall, the bottom wall between the first and second extended edges, the first extended edge on the second extending edge at the tail, the first and second extending edges disposed to form a U-shaped one piece floor engagement portion on he tail, the tail on the base, the tail spaced from the front wall, the hollow back in fluid communication with the hollow base,
    a control panel in the hollow body; and an actuator in the hollow body, the actuator in communication with the control panel.

2. The rocker of claim 1, further comprising an access port in the bottom wall and a ballast cover on the access port, the access port in fluid communication with the hollow base.

3. The rocker of claim 1, further comprising a biometric sensor on the seat, the biometric sensor attached to the control panel.

4. The rocker of claim 2, further comprising a mechanical sensor sensing movement angle, velocity and acceleration.

5. The rocker of claim 1, wherein the actuator is a noise generator.

6. The rocker of claim 2, further comprising an isolation panel removably attached to the back, the isolation panel spaced from the seat.

7. The rocker of claim 6, wherein the isolation panel further comprises a speaker connected to the control panel.

8. The rocker of claim 2, wherein the actuator is a heater connected to the control panel.

9. The rocker of claim 3, wherein the biometric sensor is adapted to sense body temperature and pulse rate of the user.

10. The rocker of claim 4, wherein the biometric sensor is adapted to sense body temperature and pulse rate of the user.

11. The rocker of claim 1, further comprising runners on the bottom wall and tamper resistant fasteners, the tamper resistant fasteners connected to the bottom wall and the runners, a rocker stop on the bottom wall.

12. The rocker of claim 8, further comprising a computer in communication with the control panel, the computer adapted to store sensor information.

13. The invention of claim 1, further comprising a rocker stop on the base.

14. A molded rocker for use by a user sitting in the rocker, the molded rocker comprising:
    a one piece hollow body comprising a hollow base, a seat and a hollow back, the hollow base having an ballast chamber and a bottom wall, an access port in the bottom wall, the seat on the hollow base, the hollow back on the seat, a U-shaped one piece floor engagement portion on the hollow base;
    a biometric sensor on the hollow body adjacent the seat;
    an actuator on the rocker, the actuator adapted to create a frequency output selected from the group of heat, vibration or light;
    a control panel, the control panel in communication with the biometric sensor and the actuator, the control panel adapted to energize the actuator, the biometric sensor attached to the control panel.

15. The rocker of claim 14, wherein the base further comprises a tail, the U-shaped one piece floor engagement portion on the hollow base on the tail, the tail adapted to limit a rocking angle.

16. The rocker of claim 14, further comprising a second biometric sensor on the rocker, the second biometric sensor attached to the control panel.

17. The rocker of claim 14, wherein the hollow body further comprises a shell, the shell formed of a translucent material, the rocker further comprising a light source in the hollow body, the light source connected to the control panel, whereby light generated by the light source in the hollow body is transmitted through the shell.

* * * * *